(12) United States Patent
Sebag et al.

(10) Patent No.: US 12,638,435 B2
(45) Date of Patent: May 26, 2026

(54) METHOD FOR THE QUANTIFICATION AND CHARACTERIZATION OF CARBON IN SOILS

(71) Applicant: IFP Energies nouvelles, Rueil-Malmaison (FR)

(72) Inventors: David Sebag, Rueil-Malmaison Cedex (FR); Isabelle Kowalewski, Rueil-Malmaison Cedex (FR); Violaine Lamoureux-Var, Rueil-Malmaison Cedex (FR); Daniel Pillot, Rueil-Malmaison Cedex (FR); Herman Ravelojaona, Rueil-Malmaison Cedex (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 273 days.

(21) Appl. No.: 18/551,018

(22) PCT Filed: Mar. 14, 2022

(86) PCT No.: PCT/EP2022/056455
§ 371 (c)(1),
(2) Date: Sep. 18, 2023

(87) PCT Pub. No.: WO2022/200091
PCT Pub. Date: Sep. 29, 2022

(65) Prior Publication Data
US 2024/0183837 A1 Jun. 6, 2024

(30) Foreign Application Priority Data
Mar. 26, 2021 (FR) ...................................... 2103112

(51) Int. Cl.
*G01N 31/12* (2006.01)
*G01N 1/44* (2006.01)
*G01N 33/24* (2006.01)

(52) U.S. Cl.
CPC ............... *G01N 33/24* (2013.01); *G01N 1/44* (2013.01)

(58) Field of Classification Search
CPC .......... G01N 33/24; G01N 1/44; G01N 31/12; G01N 33/241; G01N 2030/8854
(Continued)

(56) References Cited

U.S. PATENT DOCUMENTS 3,953,171 A 4/1976 Espitalie et al.
4,352,673 A * 10/1982 Espitalie ................ G01N 31/12
436/160

FOREIGN PATENT DOCUMENTS

FR 2227797 A5 11/1974
FR 2472754 A1 7/1981
(Continued)

OTHER PUBLICATIONS

Behar F., Beaumont V., De B., Penteado H.L. (2001) Rock-Eval 6 Technology: Performances and Developments, Oil & Gas Science and Technology 56, 111-134.
(Continued)

*Primary Examiner* — Robert R Raevis
(74) *Attorney, Agent, or Firm* — Fitch, Even, Tabin & Flannery LLP

(57) ABSTRACT

The invention relates to a method of characterizing and of quantifying carbon in a superficial deposit. The sample of the formation is subjected to heating in an inert atmosphere
(Continued)

with at least six isothermal stages connected by a thermal gradient, the sample residue is subjected to heating in an oxidizing atmosphere, and the quantities of HC, CO and $CO_2$ released during heating are measured. A ratio of the mineral carbon to the total carbon of the sample is determined, and the at least one of the organic carbon and mineral carbon content of the sample is determined according to this ratio: (i) by accounting for an estimated quantity of $CO_2$ released by thermal cracking of the organic matter of the sample during heating in the inert atmosphere if the ratio is substantially non-zero; (ii) if the ratio is substantially zero and the mineral carbon content is zero.

20 Claims, 6 Drawing Sheets

(58) Field of Classification Search
USPC .. 73/19.01, 19.12, 23.2, 23.31, 863.11, 866; 422/68.1, 78, 30
See application file for complete search history.

(56) References Cited

FOREIGN PATENT DOCUMENTS

| | | |
|---|---|---|
| FR | 3072173 A1 | 4/2019 |
| WO | 2015084784 A1 | 6/2015 |

OTHER PUBLICATIONS

Disnar, J.R., Guillet, B., Keravis, D., Di-Giovanni, C., Sebag, D., 2003. Soil organic matter (SOM) characterization by Rock-Eval pyrolysis: scope and limitations. Organic Geochemistry 34, 327-343.

Malou, O.P., Sebag, D., Moulin P., Chevallier, T., Badiane-Ndour, N.Y., Thiam, A., Chapuis-Lardy, L. 2020. The Rock-Eval® signature of soil organic carbon in Arenosols of the Senegalese groundnut Basin. How do agricultural practices matter? » Agriculture, Ecosystems & Environment 301: 107030. https://doi.org/10.1016/j.agee.2020.107030.

Pilot, D., Deville, E., Prinzhofer, A., 2014. Identification and Quantification of Carbonate Species Using Rock-Eval Pyrolysis. Oil & Gas Science and Technology—Revue d'IFP Energies nouvelles 69, 341-349.

Sebag, D., Disnar, J.R., Guillet, B., Di Giovanni, C., Verrecchia, E.P., Durand, A., 2006. Monitoring organic matter dynamics in soil profiles by "Rock-Eval pyrolysis": bulk characterization and quantification of degradation. European Journal of Soil Science 57, 344-355.

Sebag, D., Verrecchia, E.P., Cécillon, L., Adatte, T., Albrecht, R., Aubert, M., Bureau, F., Cailleau, G., Copard, Y., Decaëns, T., Disnar, J.-R., Hetényi, M., Nyilas, T., Trombino, L., 2016. Dynamics of soil organic matter based on new Rock-Eval indices. Geoderma 284, 185-203.

International Search Report for PCT/EP2022/056455, dated May 9, 2022; 4 pages.

Written Opinion for PCT/EP2022/056455, 6 pages.

* cited by examiner

[Fig. 1]
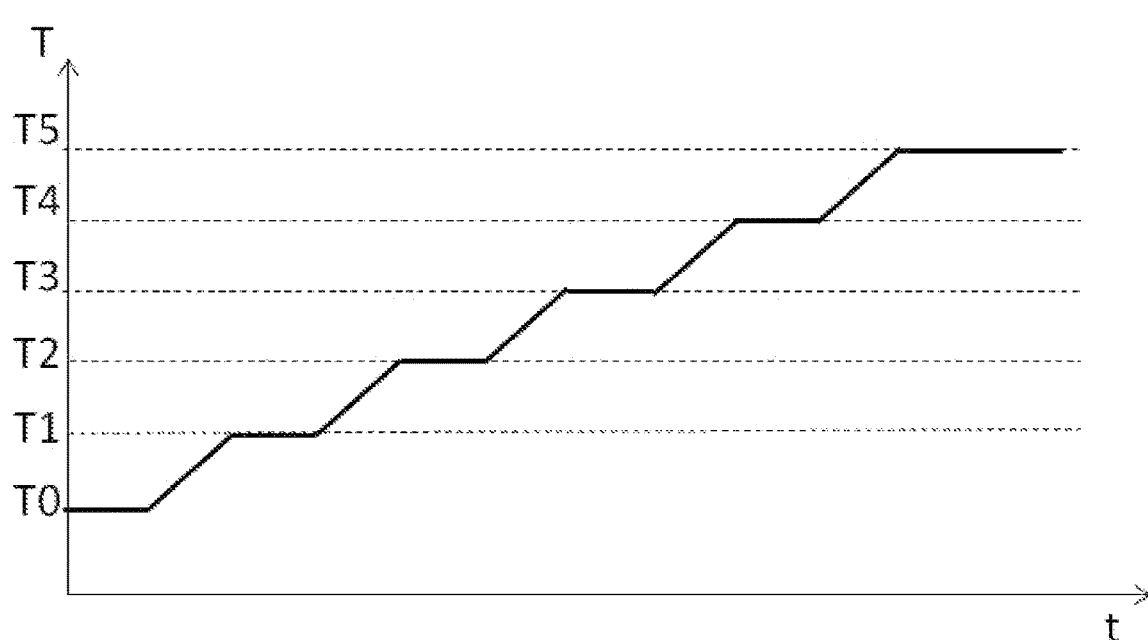
[Fig. 2A]
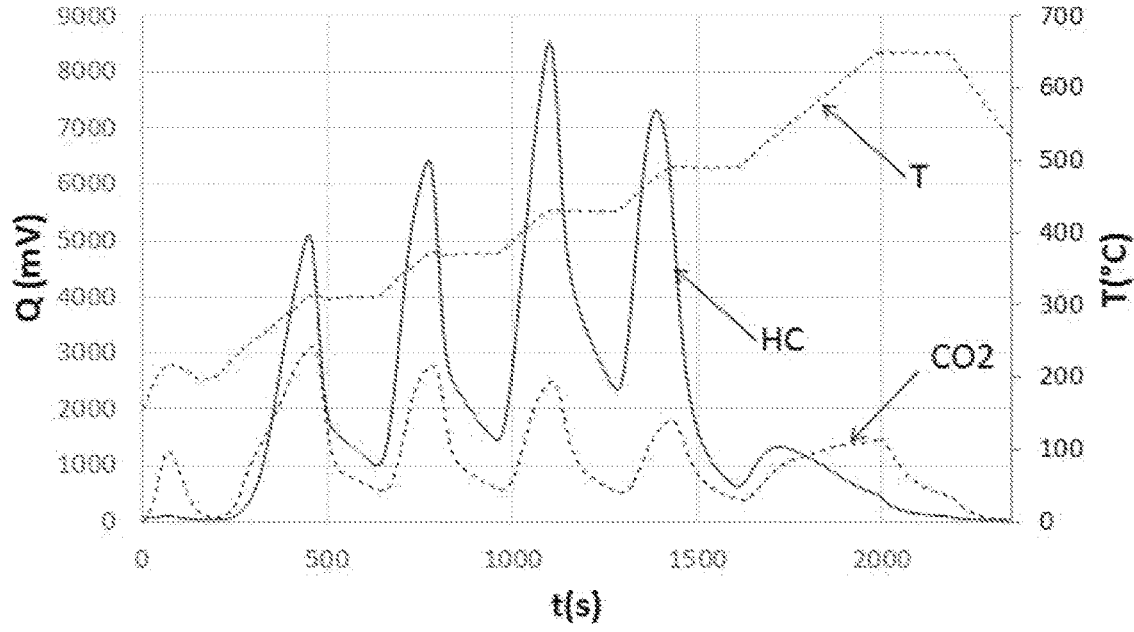

[Fig. 2B]
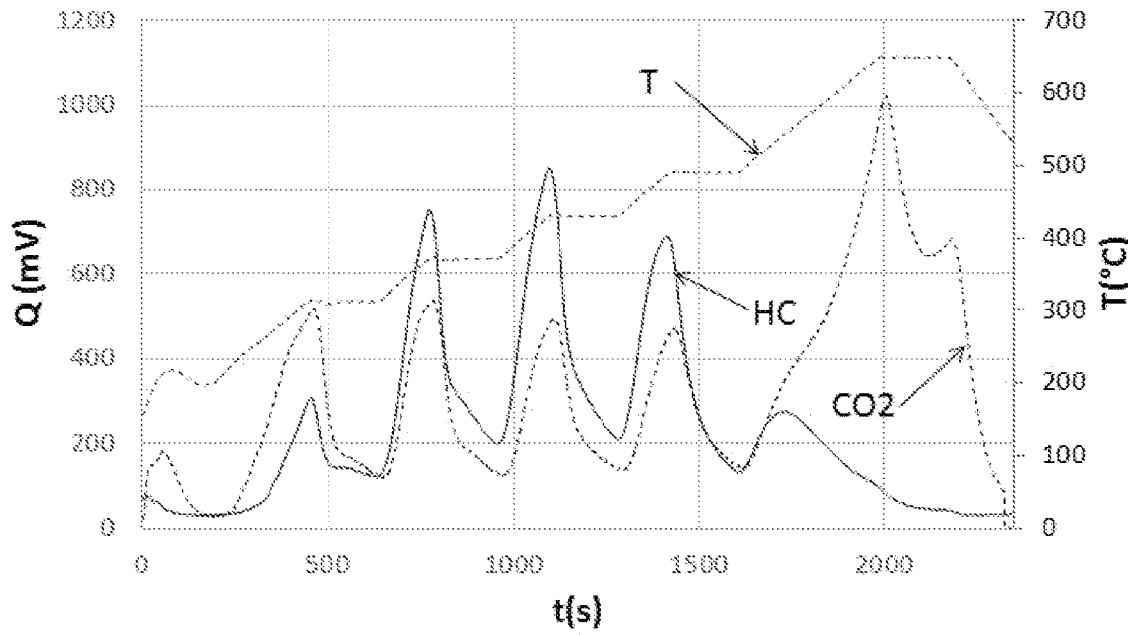
[Fig. 2C]
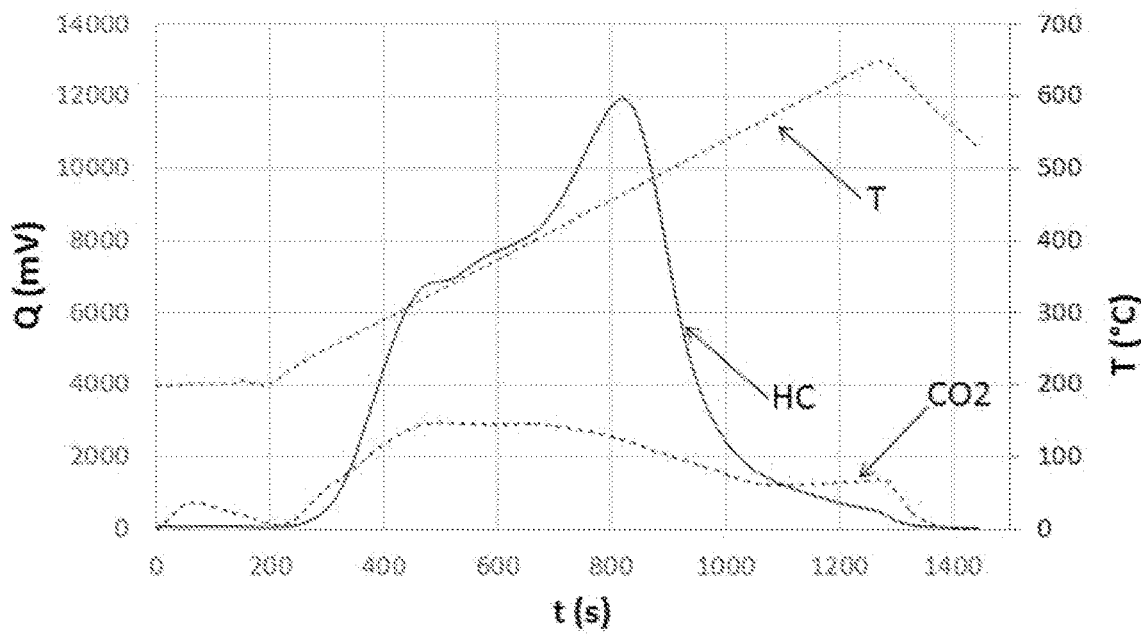

[Fig. 2D]
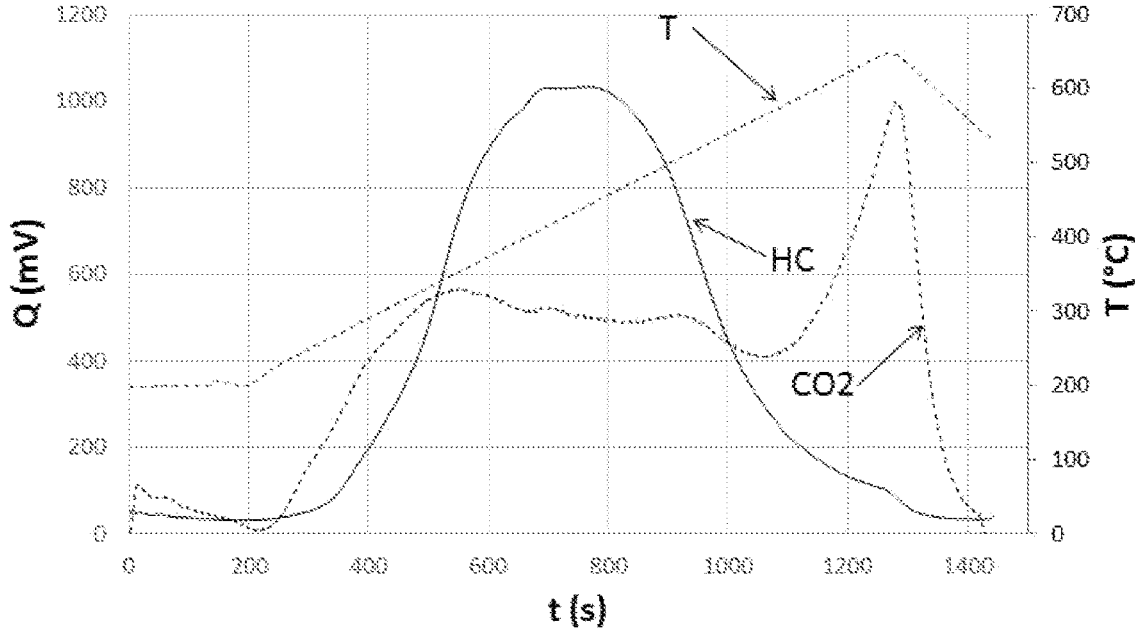
[Fig. 3A]
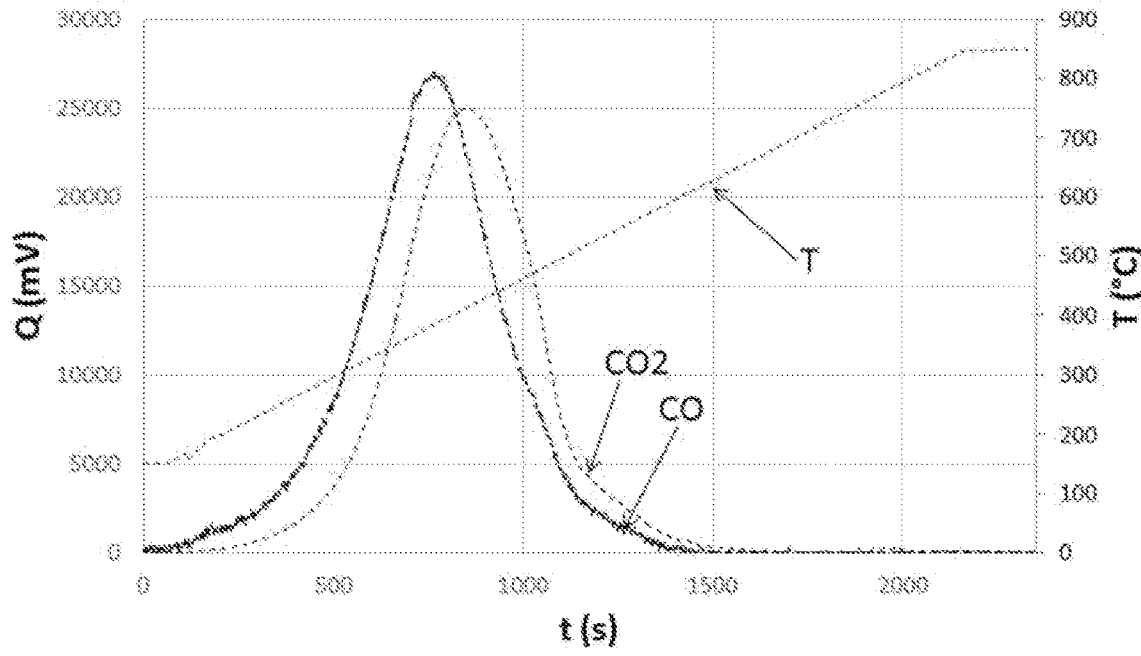

[Fig. 3B]
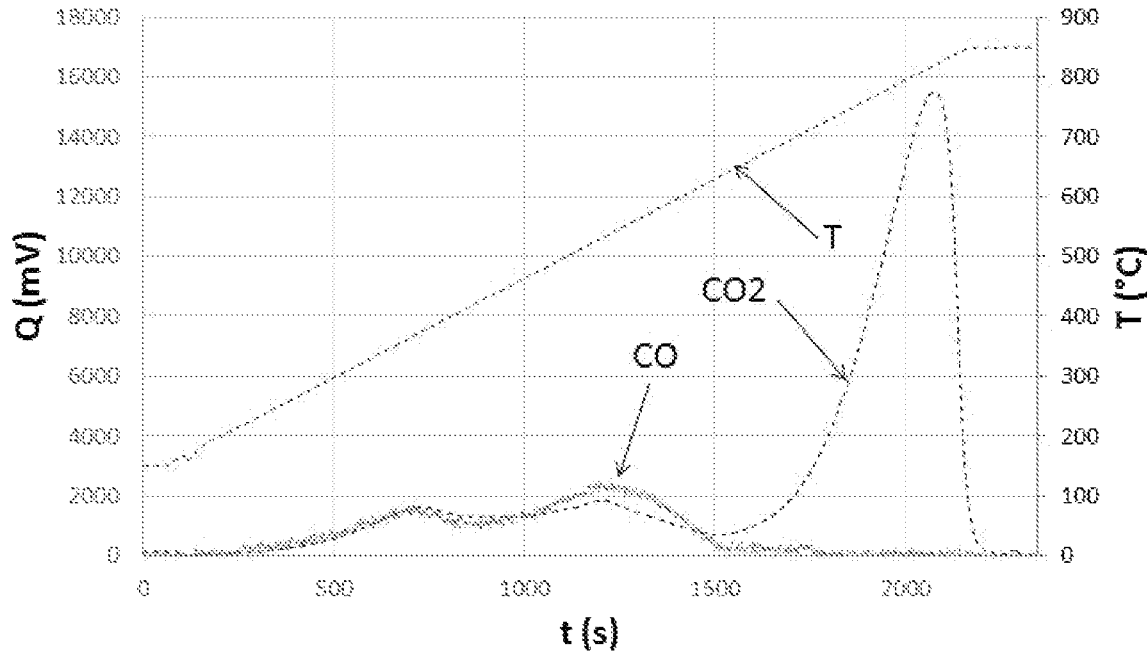
[Fig. 4A]
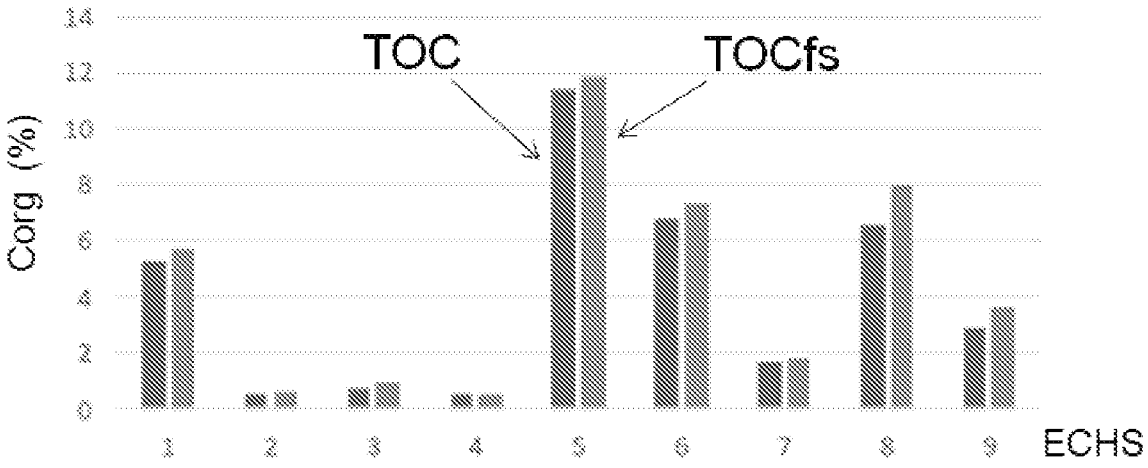

[Fig. 4B]
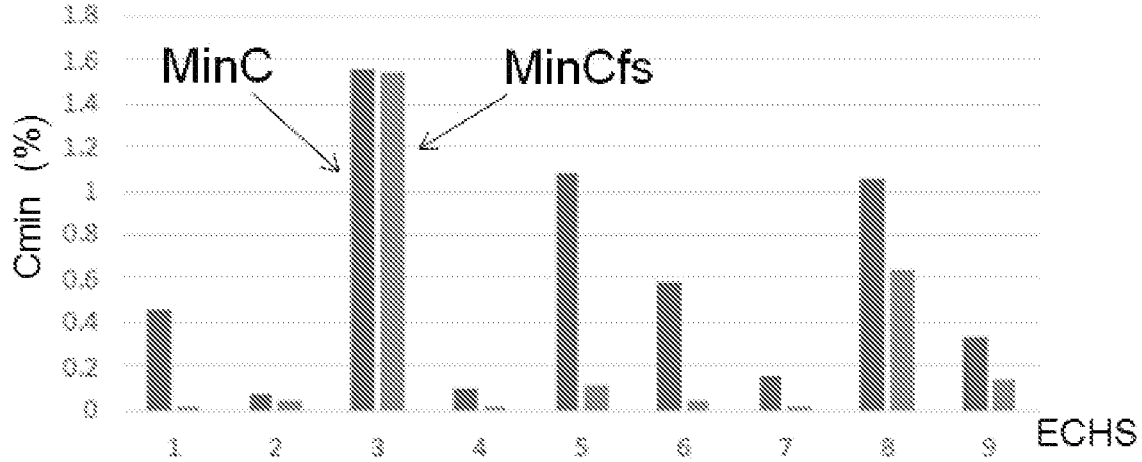
[Fig. 5A]
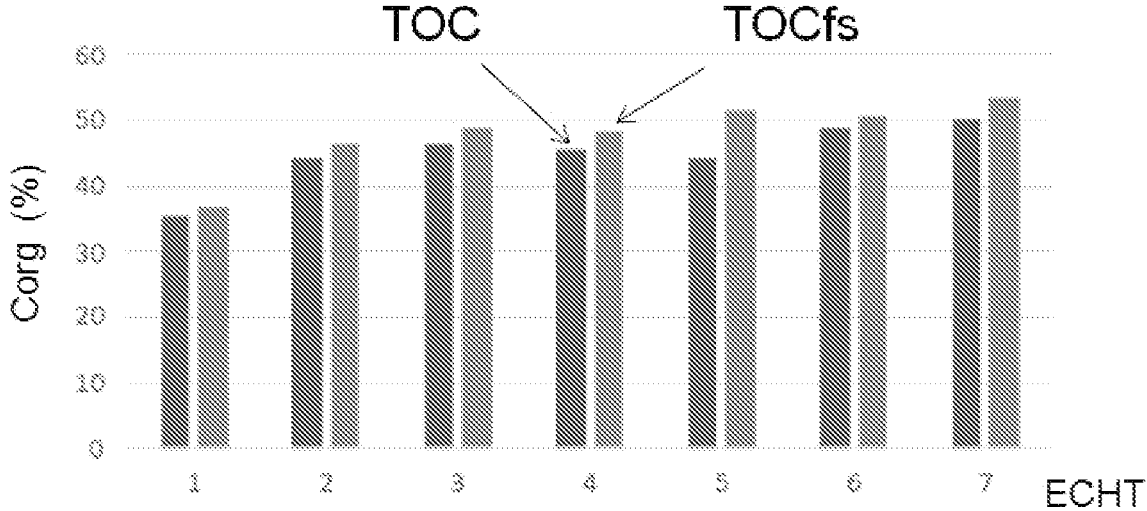

[Fig. 5B]
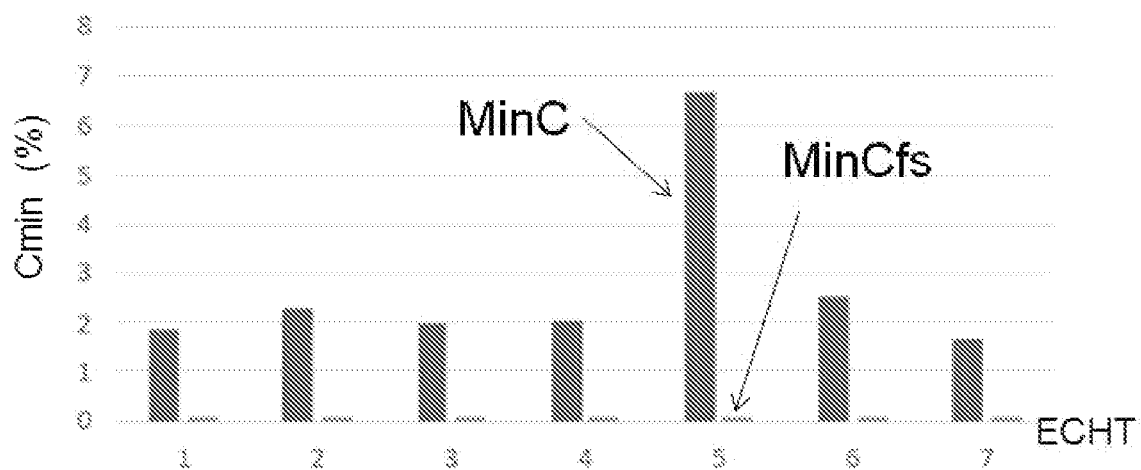

METHOD FOR THE QUANTIFICATION AND CHARACTERIZATION OF CARBON IN SOILS

CROSS-REFERENCE TO RELATED APPLICATIONS

Reference is made to PCT/EP2022/056455 filed Mar. 14, 2022, and French Patent Application No. 2103112 filed Mar. 26, 2021, which are incorporated herein by reference in their entirety.

BACKGROUND OF THE INVENTION

Field of the Invention

The present invention relates to the field of soil science and environmental geosciences. More specifically, it concerns the characterization of carbon contained in superficial deposits, and notably in soils.

Description of the Prior Art

In order to meet ecological challenges or to comply with some environmental laws or directives, professionals in the field of soil science and environmental geosciences (research laboratories, design offices, environmental agencies, farm operators) are increasingly led to establish protocols for monitoring the impact of human activities on carbon stocks in soils and in eco-agrosystems. These impact studies and monitoring require the ability to study large sample series in relatively short times in relation to conventionally employed methodologies. In addition, these methods are often accompanied by environmental and security constraints that increase the deadlines and the analytical costs which often require hiring a specialized service provider (analysis laboratories for example).

The organic forms of carbon stored in superficial deposits, notably in soils, represent a major challenge for agriculture and climate. Indeed, they play a key role on the structural quality and the fertilizing value of soils and they are notably involved in the carbon cycle by representing the largest reservoir of the Earth's organic carbon. Ensuring the food security of populations and promoting organic carbon sequestration in soils requires finding a compromise between maintaining organic matter stocks labile enough to release the nutrients needed for plant growth and promoting the storage of carbon forms resistant enough to mitigate in the long term the anthropogenic emissions of greenhouse gases.

Inorganic forms of carbon are of variable mineralogy. Essentially represented by calcium (Ca) carbonates and oxalates in soils, inorganic forms may sometimes involve other cations (Fe in siderite, Mg in dolomite, etc.), notably in a tropical environment. Irrespective of their role in biogeochemical cycles (notably as carbon sinks), the mineral forms of carbon pose technical problems for the analysis of organic forms. Indeed, no routine method makes it possible to characterize the various carbon forms with a single measurement, and the conventionally employed approaches are based on specific extractions and separations (acid fumigation, Walkley-Black method, Bernard calcimeter method), followed by targeted analyses using specialized scientific equipment (CHN elemental analysis, IR spectrometry, GC-MS, 13C-NMR).

Methods for thermal analysis of the organic matter of soils based on measurements of quantities of at least one of hydrocarbon compounds (HC), of carbon monoxide (CO), carbon dioxide ($CO_2$) released over time by a sample subjected to a heating sequence in an inert atmosphere and a heating sequence in an oxidizing atmosphere, are also known. These methods were initially developed in the oil industry for the purposes of characterization of the organic fraction of sedimentary rocks. The ROCK-EVAL® device (IFP Energies nouvelles, France) developed by the applicant and notably described in patents FR-2,227,797 (U.S. Pat. No. 3,953,171) and FR-2,472,754 (U.S. Pat. No. 4,352,673) is thus known, which comprises a pyrolysis oven distinct from an oxidation oven, a flame ionization type detector (FID) for detecting hydrocarbon compounds (HC) and an infrared type detector (IR) for detecting at least one of carbon monoxide (CO) and carbon dioxide ($CO_2$). Methods developed for particular applications in the oil industry, each having at least one of their own heating temperature sequence for pyrolysis and heating in an oxidizing atmosphere, are also known.

The ROCK-EVAL® BULK ROCK method, more particularly dedicated to conventional mother rock samples (Behar et al., 2001), is notably known. The inert-atmosphere heating sequence of this method is characterized by an initial temperature T1 of the pyrolysis oven generally ranging between 300° C. and 350° C., a temperature that is maintained for a predetermined period of time of a few minutes. It is during this phase that the so-called "free" hydrocarbons (actually corresponding to hydrocarbons of low to high molecular weight) initially contained in the rock sample are released. Their quantity is assessed by measuring the area of a first peak, denoted by S1, of the curve (also referred to as thermogram) representing the quantity of hydrocarbon compounds released during the heating sequence in an inert atmosphere. The pyrolysis temperature is subsequently increased progressively up to a temperature T2 of generally 650° C. During this phase, volatilization of the very heavy hydrocarbon compounds and cracking of the non-volatile organic matter (kerogen) take place. The quantity of hydrocarbon compounds released during this thermal cracking phase is assessed by measuring the area of a second peak, denoted by S2. In parallel, the quantities of CO and $CO_2$ are measured and also represented in form of curves. These curves have two peaks conventionally denoted by S3CO (respectively S3 $CO_2$), considered to correspond to the CO (respectively the $CO_2$) generated by cracking the organic matter of the sample during heating in an inert atmosphere, and S3'CO (respectively S3' $CO_2$), considered to correspond to the CO (respectively the $CO_2$) generated by the thermal decomposition of the carbonate forms (notably calcite) during heating in an inert atmosphere. The sample residue resulting from heating in an inert atmosphere is then subjected to heating in an oxidizing atmosphere: from a temperature ranging between about 300° C. and 400° C., preferably equal to 300° C., the temperature of the sample residue considered is raised according to a temperature gradient ranging between 20° C. and 40° C./min, up to an oxidation end temperature ranging between 750° C. and 950° C., preferably equal to 850° C. During this heating sequence in an oxidizing atmosphere, the quantities of CO and of $CO_2$ released by the sample residue are measured and represented in form of curves, leading to a peak conventionally denoted by S4CO (respectively S4 $CO_2$), considered to correspond to the quantity of CO (respectively $CO_2$) generated by the combustion of the organic matter during the oxidation cycle. From these measurements, this method defines a certain number of standard parameters, in particular the parameter denoted by TOC (Total Organic Carbon), which corresponds to the carbon content of the sample, determined from the total quantity of HC released by the sample and the quantities of CO and $CO_2$ released below threshold temperatures during the pyrolysis phase and the oxidation phase; and the parameter denoted by MinC (Mineral Carbon), which corresponds to the mineral carbon content of the sample, determined from the quantities of CO and $CO_2$ released by the sample above threshold temperatures during the pyrolysis phase and the oxidation phase.

The following documents are mentioned in the description:

Behar F., Beaumont V., De B., Penteado H. L. (2001) Rock-Eval 6 Technology: Performances and Developments, Oil & Gas Science and Technology 56, 111-134.

Disnar, J. R., Guillet, B., Keravis, D., Di-Giovanni, C., Sebag, D., 2003. Soil Organic Matter (SOM) Characterization by Rock-Eval pPyrolysis: Scope and Limitations. Organic Geochemistry 34, 327-343.

Malou, O. P., Sebag, D., Moulin P., Chevallier, T., Badiane-Ndour, N. Y., Thiam, A., Chapuis-Lardy, L. 2020. The Rock-Eval® Signature of Soil Organic Carbon in Arenosols of the Senegalese Groundnut Basin. How do agricultural practices matter?Agriculture, Ecosystems & Environment 301: 107030. https://doi.org/10.1016/j.agee.2020.107030.

Pillot, D., Deville, E., Prinzhofer, A., 2014. Identification and Quantification of Carbonate Species Using Rock-Eval Pyrolysis. Oil & Gas Science and Technology—Revue d'IFP Energies nouvelles 69, 341-349.

Sebag, D., Disnar, J. R., Guillet, B., Di Giovanni, C., Verrecchia, E. P., Durand, A., 2006. Monitoring Organic Matter Dynamics in Soil Profiles by "Rock-Eval pyrolysis": Bulk Characterization and Quantification of Degradation. European Journal of Soil Science 57, 344-355.

Sebag, D., Verrecchia, E. P., Cecillon, L., Adatte, T., Albrecht, R., Aubert, M., Bureau, F., Cailleau, G., Copard, Y., Decaens, T., Disnar, J.-R., Hetenyi, M., Nyilas, T., Trombino, L., 2016. Dynamics of Soil Organic Matter Based on New Rock-Eval indices. Geoderma 284, 185-203.

Since the 2000s, this type of analyses has also been used and adapted to study the organic fraction of superficial deposits and notably of soils.

For example, prior art knows the method described in the document (Disnar et al., 2003), which provides an adaptation of the pyrolysis heating sequence consisting of an initial temperature of the inert-atmosphere heating sequence of 200° C., instead of 300° C. in the ROCK-EVAL® BULK ROCK method described above. This lower initial temperature allows extending peak S2 defined above to the cracking temperatures of the most thermolabile organic components. Indeed, these thermolabile constituents are much more abundant in superficial deposits than in sedimentary rocks. To assess their contribution and thus to evaluate the thermal stability of the organic matter, this method defines the parameter R400 that measures the relative proportion of peak S2 corresponding to the temperatures below 400° C. Besides, this document also highlights a negative difference between parameter TOC as defined in the ROCK-EVAL® BULK ROCK method and the organic carbon contents measured with standardized methods (elemental analyses for example), and it recommends a statistical correction (i.e. application of a correction coefficient established on a representative panel of soil samples) to correct parameter TOC, defined for the oil industry, so that it is really representative of the organic carbon content, notably for samples rich in poorly decomposed organic matter in relation to their biogenic precursors (litters, composts, peat, etc.).

Also known is the document (Sebag et al., 2006), which uses this adapted heating sequence and provides in addition a deconvolution of peak S2 to assess the degree of decomposition of the organic constituents. Indeed, the thermograms of the superficial deposits, in particular of organic samples, show a plurimodal distribution whose major modes always are in particular temperature ranges (300-320° C.; 360-380° C.; 420-440° C.; 470-490° C. and 540-560° C.). The method described in this document decomposes peak S2 into five elementary Gaussian distributions centered on these modes. This mathematical deconvolution amounts to assessing the relative contribution to peak S2 of each elementary distribution considered as relative to a class of constituents defined by their only cracking temperature. These elementary contributions are subsequently used to calculate new parameters that measure the overall thermal stability of the organic matter (R-index) and the degree of decomposition of the thermolabile fraction (I-index). However, the deconvolution method is based on an iterative approach for adjusting the position and the area of each elementary distribution according to arbitrarily set statistical parameters, which reduces the reproducibility of the decomposition.

Prior art also knows the document (Sebag et al., 2016), which describes an alternative approach showing that an integration of the thermograms representative of the quantity of HC contained in the sample by temperature bands (200-340° C.; 340-400° C.; 400-460° C.; 460-520° C. and 520-650° C.) which leads to results comparable to the mathematical deconvolution, which are, moreover, perfectly reproducible. This approach has been used for many applications, but it suffers from some intrinsic limits. First, it is based on the definition of empirically defined threshold temperatures, so that the area of each temperature band best approximates the area of the corresponding elementary distribution obtained by deconvolution. Besides, these areas and the parameters resulting therefrom only provide qualitative information insofar as they all correspond to relative proportions or to relative proportion ratios. Finally, this approach is limited to the consideration of the quantities of HC emitted during the pyrolysis phase, whereas the majority of the carbon is represented by the CO and the $CO_2$ emitted during the pyrolysis and oxidation phases.

Furthermore, despite these adaptation or improvement attempts, the known methods do not provide standard parameter values TOC and MINC respectively representative of the organic carbon and mineral carbon content of a sample in the case of superficial deposits. Indeed, parameter TOC (respectively MINC) of the ROCK-EVAL® BULK ROCK method measures the carbon content from the quantities of CO and $CO_2$ released below (respectively above) threshold temperatures considered as thermal limits between the organic and mineral forms of carbon.

Now, this definition is inaccurate, whether for carbonate or non-carbonate formations. Indeed, as shown in the document (Malou et al., 2020), this definition notably involves the systematic calculation of a parameter MINC, even for samples with no mineral carbon form. However, more generally, as observed by the applicant, this implies that, even in samples containing mineral carbon forms, a part of parameter MINC results from the thermal cracking of organic constituents above threshold temperatures. Finally, as shown in the document (Pillot et al., 2014), some mineral forms of carbon (such as siderite or oxalates) are likely to decompose at temperatures below the threshold temperatures used for calculating the standard parameters TOC and MINC.

SUMMARY OF THE INVENTION

The present invention aims to overcome the drawbacks related to the use of a method initially developed for the oil industry for analysis of the organic matter in superficial deposits, and notably in soils. In particular, the present invention aims to obtain thermograms showing better differentiated peaks, common to each type of effluent (HC, CO and CO). This invention thus allows better discrimination between the different compound classes depending on their thermal resistance. It also leads to determination of organic and mineral nature of carbon forms, and thereby to define new parameters, more representative of the organic and mineral carbon content of samples analyzed with standardized methods.

More generally, the present invention enables fast and reliable characterization of the carbon forms present in a sample, in order to determine whether they contain forms of mineral nature or not, to specify at least one of the degree of decomposition and the thermal stability of the most reactive organic matter part (bonded to the hydrogen atom), and to quantify more precisely the carbon contents (organic vs. mineral, thermolabile vs. thermostable).

The present invention relates to a method of characterizing and quantifying the carbon present in a superficial deposit, from a sample representative of the superficial deposit, wherein at least the following steps are applied to the sample:

A. heating the sample according to a first heating sequence in an inert atmosphere, and continuously measuring a quantity of hydrocarbon compounds, a quantity of CO and a quantity of $CO_2$ released during the first heating sequence, the first heating sequence in an inert atmosphere comprising at least a succession of at least six isothermal stages of predetermined duration, the succession of the at least six isothermal stages comprising a first isothermal stage at a first temperature ranging between 80° C. and 200° C. (TO), a second isothermal stage at a second temperature ranging between 340° C. and 380° C. (T1), a third isothermal stage at a third temperature ranging between 400° C. and 440° C. (T2), a fourth isothermal stage at a fourth temperature ranging between 450° C. and 490° C. (T3), a fifth isothermal stage at a fifth temperature ranging between 500° C. and 540° C. (T4), and a sixth isothermal stage at a sixth temperature ranging between 580° C. and 650° C. (T5), with the isothermal stages being connected by a thermal gradient;

B. heating a residue of the sample from the first heating sequence according to a second heating sequence in an oxidizing atmosphere, and measuring a quantity of CO and a quantity of $CO_2$ released during the second heating sequence, the second heating sequence in an oxidizing atmosphere starting at a minimum temperature ranging between 150° C. and 300° C., and ending at a maximum temperature ranging between 850° C. and 1200° C., following a thermal gradient;

C. determining a value of a parameter SCmin representative of a mineral carbon proportion in relation to the total carbon of the sample, from a ratio between the quantity of $CO_2$ released by the residue of the sample above an intermediate temperature of the second heating sequence ranging between 620° C. and 680° C., and the quantity of $CO_2$ released by the residue during the second heating sequence;

D. quantifying at least one of an organic carbon content and a mineral carbon content of the sample as follows:

i. if the value of the parameter SCmin is less than or equal to a predefined threshold value of the parameter SCmin, the mineral carbon content is zero and the organic carbon content depends on the totality of the quantities of HC, CO and $CO_2$ released during the first heating sequence, and of the quantities of CO and $CO_2$ released during the second heating sequence up to the intermediate temperature of the second heating sequence;

ii. if the value of the parameter SCmin is greater than the predefined threshold value of the parameter SCmin:

a quantity of $CO_2$ released by thermal cracking of the organic matter of the sample during the first heating sequence above the third temperature (T2) is estimated from the quantity of $CO_2$ released during the first heating sequence up to the third temperature (T2) of the first heating sequence, multiplied by at least one of a predefined factor k, and the organic carbon content and/or the mineral carbon content is determined according to the quantities of HC, CO and $CO_2$ released during the first heating sequence and to the quantities of CO and $CO_2$ released during the second heating sequence up to the intermediate temperature of the second heating sequence, and by taking into account the estimated quantity of $CO_2$ released by thermal cracking of the organic matter of the sample during the first heating sequence above the third temperature (T2).

According to an implementation of the invention, if the value of the parameter SCmin is greater than the predefined threshold value of the parameter SCmin:

the organic carbon content can depend on the totality of the quantity of HC released during the first heating sequence, on the quantity of CO released during the first heating sequence up to the fifth temperature (T4), to which half of the quantity of CO released during the first heating sequence above the fifth temperature (T4) is added, on the quantity of $CO_2$ released during the first heating sequence up to the third temperature (T2), to which the estimated quantity of $CO_2$ released by thermal cracking of the organic matter of the sample during the first heating sequence above the third temperature (T2) is added, and on the quantities of CO and $CO_2$ released during the second heating sequence up to the intermediate temperature of at least one of the second heating sequence, and the mineral carbon content can depend on the quantity of $CO_2$ released during the first heating sequence above the third temperature (T2) of the first heating sequence, from which the estimated quantity of $CO_2$ released by thermal cracking of the organic matter of the sample during the first heating sequence above the third temperature (T2) is subtracted, on the half of the quantity of CO released during the first heating sequence above the fifth temperature (T4), and on the quantity of $CO_2$ released during the second heating sequence above the intermediate temperature of the second heating sequence.

According to an implementation of the invention, the predefined factor k can range between 1.3 and 1.4, and it is preferably equal to 1.3724.

According to an implementation of the invention, using samples from non-carbonate superficial deposits, at least the first heating sequence can be applied to each of the samples of the plurality of samples, a quantity of $CO_2$ released by each of the samples during the first heating sequence can be measured, and the factor k can be determined by means of a linear regression applied between the quantities of $CO_2$ released by the samples up to the third temperature (T2) of the first heating sequence and the quantities of $CO_2$ released by the samples above the third temperature (T2) of the first heating sequence.

According to an implementation of the invention, the predefined threshold value of the parameter SCmin can range between 0.03 and 0.05, and it is preferably equal to 0.04.

According to an implementation of the invention, the first temperature (TO) of the first heating sequence can range between 80° C. and 150° C., and it is preferably equal to 150° C.

According to an implementation of the invention, the minimum temperature of the second heating sequence can be equal to the first temperature (TO) of the first heating sequence.

According to an implementation of the invention, the predetermined duration of one of the isothermal stages of the first heating sequence can range between 3 and 5 minutes.

According to an implementation of the invention, one of the thermal gradients of the first heating sequence can range between 1° C. and 50° cmin−1, and preferably is between 20° C. and 25° cmin−1.

According to an implementation of the invention, the thermal gradient of the second heating sequence can range between 20° C. and 40° cmin−1, preferably between 20° C. and 25° cmin−1.

According to an implementation of the invention, if the value of the parameter SCmin is less than or equal to the predefined threshold value of the parameter SCmin:

the mineral carbon content can be defined by a parameter MinCfs such that at least one of MinCfs=0; and the organic carbon content can be defined by a parameter TOCfs expressed according to a formula of:

$$TOCfs = (S2_t \times 0.083) + \left(S3CO2_t \times \frac{12}{440}\right) + \left(S3CO_t \times \frac{12}{280}\right) + \left(S4CO2_a \times \frac{12}{440}\right) + \left(S4CO_a \times \frac{12}{280}\right)$$

where $S2_t$, $S3CO2_t$, $S3CO_t$ respectively represent the quantities of HC, $CO_2$ and CO released during the first heating sequence, $S4CO2_a$ and $S4CO_a$ respectively represent the quantities of $CO_2$ and CO released during the second heating sequence and up to the intermediate temperature of the second heating sequence.

According to an implementation of the invention, if the value of the parameter SCmin is greater than the predefined threshold value of the parameter SCmin:

the mineral carbon content can be defined by a parameter MinCfs expressed according to a formula of the type:

$$MinCfs = \left([S3CO2_b - S3CO2_c] \times \frac{12}{440}\right) + \left(1/2S3CO_b \times \frac{12}{280}\right) + \left(S4CO2_b \times \frac{12}{440}\right)$$

where $S3CO2_b$ represents the quantity of $CO_2$ released during the first heating sequence above the third temperature (T2), $S3CO2_c$ represents the estimated quantity of $CO_2$ released by thermal cracking of the organic matter of the sample during the first heating sequence above the third temperature (T2), $S3CO_b$ represents the quantity of CO released during the first heating sequence above the fifth temperature (T4), and $S4CO2_b$ represents the quantity of $CO_2$ released during the second heating sequence above the intermediate temperature of the second heating sequence; and at least one of the organic carbon content can be defined by a parameter TOCfs expressed according to a formula of the type:

$$TOCfs = (S2_t \times 0.083) + \left([S3CO2_a + S3CO2_c] \times \frac{12}{440}\right) + \left([S3CO_a + 1/2S3CO_b] \times \frac{12}{280}\right) + \left(S4CO2_a \times \frac{12}{440}\right) + \left(S4CO_a \times \frac{12}{280}\right)$$

where $S2_t$ represents the quantity of HC released during the first heating sequence, $S3CO2_a$ represents the quantity of $CO_2$ released during the first heating sequence up to the third temperature (T2), $S3CO2_c$ represents the estimated quantity of $CO_2$ released by thermal cracking of the organic matter of the sample during the first heating sequence above the third temperature (T2), $S3CO_a$ and $S3CO_b$ represent the quantities of CO released during the first heating sequence respectively up to and above the fifth temperature (T4), $S4CO2_a$ and $S4CO_a$ respectively represent the quantities of $CO_2$ and CO released during the second heating sequence and up to the intermediate temperature of the second heating sequence.

BRIEF DESCRIPTION OF THE DRAWINGS

Other features and advantages of the method according to the invention will be clear from reading the description hereafter of embodiments given by way of non-limitative example, with reference to the accompanying figures wherein:

FIG. 1 schematically illustrates the heating sequence in an inert atmosphere according to the invention;

FIGS. 2A and 2B illustrate thermograms obtained with an implementation of the heating sequence in an inert atmosphere according to the invention, obtained for a non-carbonate soil sample and a carbonate soil sample respectively;

FIGS. 2C and 2D illustrate thermograms obtained with a heating sequence according to the prior art, obtained for the non-carbonate soil and carbonate soil samples of FIGS. 2A and 2B respectively;

FIGS. 3A and 3B illustrate thermograms obtained with an implementation of the heating sequence in an oxidizing atmosphere according to the invention, obtained for the non-carbonate soil sample of FIGS. 2A and 2C, and for the carbonate soil sample of FIGS. 2B and 2D respectively;

FIGS. 4A and 4B show histograms comparing respectively the values of the organic carbon contents Corg and of the mineral carbon contents Cmin determined with the method according to the invention and according to the prior art, for 9 soil samples; and FIGS. 5A and 5B show histograms comparing respectively the values of the organic carbon contents Corg and of the mineral carbon contents Cmin determined with the method according to the invention and according to the prior art, for 7 peat samples.

DETAILED DESCRIPTION OF THE INVENTION

The invention relates to a method of characterizing and quantifying the carbon (or, in other words, the carbon forms) present in a superficial deposit.

A superficial deposit is understood to be a continental or littoral formation, unconsolidated or with secondary consolidation, resulting from at least one of the mechanical and chemical weathering of pre-existing rocks, and formed at the lithosphere/biosphere/atmosphere interface. One distinguishes (i) the "allochthonous superficial deposits" (such as colluvium, alluvium, loess, etc.), which have undergone or still undergo close or distant displacements, and no longer rest on their parent material, and (ii) the "autochthonous superficial deposits" (such as grits, alterites, flint clays, etc.), which have evolved locally, from a parent material that still is their substrate.

Soil is understood to be all of the outer layers of superficial deposits, whose properties are directly controlled by the mutual actions of water, air and of living and dead organisms, or even human activities for the most recent periods.

These terms are notably defined in the reference document (Dictionnaire encyclopedique de Science du Sol, Mathieu & Lozet, Lavoisier, 2011).

The method according to the invention requires at least one sample representative of the superficial deposit. This sample may have been taken manually in a trough or by core drilling using an auger bit. Advantageously, the sample as taken is sieved using a sieve with 2 mm diameter orifices, dried at a temperature below 40° C., then crushed until fragments of size less than 200 µm are obtained.

The method according to the invention can advantageously, but without limitation, be implemented using the ROCK-EVAL® device (IFP Energies nouvelles, France) as described in patents FR-2,227,797 (U.S. Pat. No. 3,953,171) and FR-2,472,754 (U.S. Pat. No. 4,352,673). Indeed, the ROCK-EVAL® device comprises at least:

an oven for pyrolysis in a non-oxidizing atmosphere;
means for transferring the pyrolysis residues to an oxidation oven;
an oven for oxidation in an oxidizing atmosphere;
means for measuring the quantity of hydrocarbon compounds (HC) released during pyrolysis; and
means for measuring the carbon monoxide (CO) and the carbon dioxide ($CO_2$).

The method can also be implemented using a single pyrolysis oven operating both in a non-oxidizing atmosphere and in an oxidizing atmosphere, cooperating with a device for measuring the quantity of hydrocarbon compounds released during pyrolysis, and a device for measuring the carbon monoxide and the carbon dioxide.

The method according to the invention comprises at least the following steps:

1—Heating sequence in an inert atmosphere (pyrolysis)
2—Heating sequence in an oxidizing atmosphere (oxidation)
3—Characterization and quantification of the carbon present in the sample.

The steps of the method according to the invention are detailed hereafter, without limitation, for a soil sample. Indeed, the steps of the method according to the invention may as well be applied to a sample from another layer of a superficial deposit.

1—Heating Sequence in an Inert Atmosphere (Pyrolysis)

In this step, a soil sample is heated in an inert atmosphere (in a stream of nitrogen, helium, for example) according to a sequence of predefined time-varying temperatures.

According to the invention, the heating sequence in an inert atmosphere comprises at least a succession of isothermal stages, each isothermal stage having a predetermined duration, and two consecutive isothermal stages in this succession of isothermal stages being connected by a ramp in a form of a predetermined thermal gradient. In other words, the heating sequence in an inert atmosphere comprises a succession of isothermal stages connected by a ramp. The duration of each isothermal stage can be different from the duration of the other isothermal stages, and the slope of a ramp can be different from the slope of the other thermal ramps.

According to the invention, the succession of isothermal stages comprises at least six isothermal stages connected by five ramps. According to the invention, the succession of isothermal stages comprises a first isothermal stage at a temperature (denoted by TO hereafter) ranging between 80° C. and 200° C., a second isothermal stage at a temperature (denoted by T1 hereafter) ranging between 340° C. and 380° C., a third isothermal stage at a temperature (denoted by T2 hereafter) ranging between 400° C. and 440° C., a fourth isothermal stage at a temperature (denoted by T3 hereafter) ranging between 450° C. and 490° C., a fifth isothermal stage at a temperature (denoted by T4 hereafter) ranging between 500° C. and 540° C., and a sixth isothermal stage at a temperature (denoted by T5 hereafter) ranging between 580° C. and 650° C.

FIG. 1 schematically illustrates such a temperature sequence by showing the evolution of temperature T as a function of time t, the temperature sequence having six isothermal stages at temperatures TO, T1, T2, T3, T4 and T5 as defined above.

According to the invention, the predetermined duration of the isothermal stages is non-zero (greater than half a minute for example), and it can preferably range between 3 and 5 minutes. Such durations allow for considering that cracking of the compounds having a cracking temperature close to the temperature of the isothermal stage is completed. In general, the duration of an isothermal stage can be different from the duration of the other isothermal stages in the heating sequence in an inert atmosphere.

Advantageously, the thermal gradient between two isothermal stages can range between 1° C. and 50° cmin$^{-1}$, which preferably ranges between 20° C. and 25° cmin$^{-1}$. Such values are compromises allowing starting of thermal cracking of the compounds associated with the isothermal stage having the highest temperature among these two isothermal stages, while limiting the duration of implementation of the method. In general, the value of a thermal gradient between two isothermal stages can be different from the other thermal gradients in the heating sequence in an inert atmosphere.

According to the invention, a quantity of hydrocarbon compounds released during heating in an inert atmosphere, and the quantity of $CO_2$ and CO contained in the effluent resulting from the heating are also continuously measured. In other words, during this sequence, the quantity of HC, CO and $CO_2$ released by the sample by thermal cracking of the organic matter and by the thermal decomposition of the carbonate minerals is continuously measured. Thus, a first curve representative of the quantity of hydrocarbon compounds released over time during at least part of the pyrolysis phase, and two other curves representative of the quantity of CO and $CO_2$ released over time during the pyrolysis phase, are obtained at the end of this step applied to a given sample. Measuring the quantity of hydrocarbon compounds can be done using a flame ionization type detector (FID). Measuring the quantity of CO and $CO_2$ released can be done using an infrared (IR) type detector. It should be noted that such detectors measure a stream of HC and at least one of CO and $CO_2$, and that they give values measured in millivolts (mV). Conventionally, a quantity of HC, CO and/or $CO_2$ can be determined by determining an area under the curve measured (possibly between predefined temperatures) by these detectors, and by dividing this area by the mass in mg of the sample. As a variant, other means of measuring the quantity of HC, CO and/or $CO_2$ can be used.

In general, this particular heating sequence in an inert atmosphere enables thermal separation of the compound classes characterized by their specific cracking temperature. Thus, compounds cracking between TO and T1 correspond to "thermally very labile compounds", which are particularly abundant in fresh biological tissues; compounds cracking between T1 and T2 correspond to "thermally labile compounds", which predominate in organic samples such as litters or peats; compounds cracking between T2 and T3 correspond to "thermally resistant compounds", predominant in organo-mineral (soils) or mineral (alluvium, colluvium) samples; compounds cracking between T3 and T4 correspond to "thermally refractory compounds"; and compounds cracking between T4 and T5 correspond to "thermally very refractory compounds", that are present in larger proportions in decomposition residues or in exogenous fractions, such as pyrogenic or petrogenic organic matter.

According to an implementation of the invention, the first isothermal stage can preferably be at a temperature ranging between 80° C. and 150° C., so as to enable recovery of the contributions of the most labile organic compounds present in a soil sample. Preferably, the first isothermal stage is at a value of 150° C., which is a sufficient temperature for recovery of the contributions of the most labile organic compounds present in most superficial deposits, notably soils.

According to an implementation of the invention, the maximum temperature T5 of the heating sequence in an inert atmosphere can preferably be 600° C. Such a temperature makes possible avoiding CO and $CO_2$ curves which have incomplete peaks at the end of pyrolysis, notably when the maximum temperature reaches 650° C., in particular with plant samples (litters, peats, composts).

According to an implementation of the invention, the succession of isothermal stages according to the invention, as described above, can be preceded by a pyrolysis oven temperature rise phase, which can be a thermal gradient ranging, for example, between 1° C. and 50° C. $cmin^{-1}$, preferably between 20° C. and 25° C. $cmin^{-1}$, or of any other form of temperature rise curve of the pyrolysis oven. This preliminary phase of pyrolysis oven temperature rise allows the pyrolysis oven to be brought to the temperature of the first isothermal stage of the heating sequence in an inert atmosphere according to the invention. This preliminary phase can contribute to starting thermal cracking of the compounds whose cracking temperature is less than the temperature of the first isothermal stage, notably in case of fresh biological tissues.

According to an implementation of the invention, the succession of isothermal stages according to the invention, as described above, can be followed by a phase of lowering the pyrolysis oven temperature, which can be a thermal gradient ranging for example between −1° C. and −50° $cmin^{-1}$, preferably between −20° C. and −25° $cmin^{-1}$, or of any other temperature decrease curve of the pyrolysis oven. This end phase of lowering the pyrolysis oven temperature enables, if need be, completing thermal cracking of the compounds associated with the last isothermal stage of the heating sequence in an inert atmosphere according to the invention.

Thus, in general, this particular heating sequence in an inert atmosphere allows thermal separation of the compound classes defined by their specific cracking temperature. This thermal fractionation notably makes possible obtaining thermograms with dissociated peaks, thus allowing independently quantifying and analyzing the streams of HC, CO and $CO_2$ released by each compound class. FIGS. 2A and 2B illustrate thermograms obtained by the heating sequence in an inert atmosphere according to the invention, for a non-carbonate soil sample and a carbonate soil sample respectively. FIGS. 2C and 2D illustrate thermograms obtained by using a heating sequence according to the prior art, with no isothermal stages, obtained for the non-carbonate and carbonate soil samples of FIGS. 2A and 2B respectively. More precisely, in these figures, curve T represents the evolution over time t of the pyrolysis oven temperature during this step or, in other words, curve T represents the heating sequence in an inert atmosphere to which the samples are subjected. It can be noted in this figure that the heating sequence in an inert atmosphere carried out for these samples comprises a preliminary phase of pyrolysis oven temperature rise, up to a temperature of the first isothermal stage of 200° C., and an end phase of lowering the pyrolysis oven temperature at the end of the last isothermal stage, at a temperature of 650° C. Moreover, curve HC represents the evolution of the intensity Q (in mV) of the signal of a detector FID measuring the quantity of hydrocarbon compounds released during the heating sequence in an inert atmosphere, and curve $CO_2$ represents the evolution of intensity Q (in mV) of the signal of a detector IR measuring the quantity of $CO_2$ released during the heating sequence in an inert atmosphere. It can be noted in FIGS. 2A and 2B that curves HC and $CO_2$ have well dissociated peaks, unlike the curves of FIGS. 2C and 2D, which shows that the multi-stage heating sequence in an inert atmosphere indeed enables thermal fractionation of the compounds contained in a sample into compound classes having their own specific cracking temperature.

It should be noted that a sensitivity analysis performed on a diverse panel of superficial deposits comprising recent soils and sediments shows that the heating sequence in an inert atmosphere according to the invention does not significantly modify the quantities of HC, CO and $CO_2$ released during pyrolysis. In other words, the total quantity of HC, CO and $CO_2$ is conserved by the heating sequence in an inert atmosphere according to the invention. On the other hand, the multi-stage heating sequence according to the invention allows better discussion of the peaks relative to distinct compound classes as discussed above.

Subsequently, the parameters defined below in Table 1 are used. More precisely, parameters $S2_i$ ($S3CO2_i$ and $S3CO_i$ respectively), with i ranging from 0 to 6, correspond to the quantities of HC (respectively $CO_2$ and CO) released in the temperature ranges $DT_i$ defined as follows: $DT_0 = T0-$; $T0 < DT_1 \leq T1$; $T1 < DT_2 \leq T2$; $T2 < DT_3 \leq T3$; $T3 < DT_4 \leq T4$; $T4 < DT_5 \leq T5$; $DT_6 = T5+$; and where TO corresponds to the first isothermal stage at temperature T0 of the heating sequence in an inert atmosphere, possibly preceded by a preliminary phase of temperature rise of the pyrolysis oven; and where T5+ corresponds to the last isothermal stage at temperature T5 of the heating sequence in an inert atmosphere, possibly followed by an end phase of lowering the pyrolysis oven temperature.

TABLE 1

| Temperature | HC measurement | $CO_2$ measurement | CO measurement |
|---|---|---|---|
| $DT_0 = T0-$ | $S2_0$ | $S3CO2_0$ | $S3CO_0$ |
| $T0 < DT_1 \le T1$ | $S2_1$ | $S3CO2_1$ | $S3CO_1$ |
| $T1 < DT_2 \le T2$ | $S2_2$ | $S3CO2_2$ | $S3CO_2$ |
| $T2 < DT_3 \le T3$ | $S2_3$ | $S3CO2_3$ | $S3CO_3$ |
| $T3 < DT_4 \le T4$ | $S2_4$ | $S3CO2_4$ | $S3CO_4$ |
| $T4 < DT_5 \le T5$ | $S2_5$ | $S3CO2_5$ | $S3CO_5$ |
| $DT_6 = T5+$ | $S2_6$ | $S3CO2_6$ | $S3CO_6$ |

2—Heating Sequence in an Oxidizing Atmosphere (Oxidation)

In this second step, the solid sample residue obtained at the end of the heating sequence in an inert atmosphere, as described in step 1 above, is subjected to oxidation according to a predefined time-varying temperature program.

The temperature program of the heating sequence in an oxidizing atmosphere according to the invention is as follows: From a temperature (T'min) ranging between 150° C. and 300° C., preferably ranging between 150° C. and 200° C., and preferably equal to 150° C. or more preferably equal to the temperature of the first isothermal stage of the heating sequence in an inert atmosphere so as to be able to make comparisons, the temperature of the sample residue from step 1 is increased according to a temperature gradient ranging between 20° C. and 40° cmin–1, preferably between 20° C. and 25° cmin–1, up to an oxidation end temperature (T'max) ranging between 850° C. and 1200° C., and preferably equal to 900° C., which is sufficient to deplete the mineral carbon stock of most superficial deposit samples.

According to the invention, a representative quantity of CO and $CO_2$ released during this second heating sequence, is continuously measured. According to an implementation of the invention, this measurement can be performed using an infrared (IR) type detector. It should be noted that such a detector measures a stream of at least one of CO and $CO_2$, and it provides values measured in millivolts (mV). Conventionally, at least one of a quantity of CO and $CO_2$ is determined by determining an area under the curve (possibly between predefined temperatures) measured by this detector with this area being divided by the mass in mg of the sample. As a variant, other devices for measuring the quantity of at least one of CO and $CO_2$ can be used.

In general, the preferred temperature range for the initial temperature of the heating sequence in an oxidizing atmosphere, which is lower than the initial temperatures known from the prior art (generally 300° C.), makes possible avoiding episodes of instantaneous combustion of the sample residue at the beginning of the oxidation cycle.

FIGS. 3A and 3B illustrate thermograms obtained by using the heating sequence in an oxidizing atmosphere according to the invention, respectively for the non-carbonate soil sample of FIGS. 2A and 2C, and for the carbonate soil sample of FIGS. 2B and 2D. More precisely, in these figures, curve T represents the evolution over time t of the oxidation oven temperature during this step or, in other words, curve T represents the heating sequence in an oxidizing atmosphere to which the sample residues are subjected. Moreover, curve $CO_2$ (respectively CO) represents the evolution of intensity QCO2 in mV (respectively QCO) of the signal of an IR detector measuring the quantity of $CO_2$ (respectively CO) released over time by the residue from step 1 which is subjected to the heating sequence in an oxidizing atmosphere T. Streams of $CO_2$ above a temperature of approximately 650° C., which are specific to carbonate soils and which represent the presence of mineral forms of carbon, can be observed in these figures.

Subsequently, the parameters defined in Table 2 below are used. More precisely, parameters $S4CO2_i$ and $S4CO_i$, with i ranging from 0 to 4, correspond to the quantities of $CO_2$ and CO released in the temperature ranges $DT'_i$ defined as follows: $DT'0 \le T'min$; $T'min < DT'1 \le T'int1$; $T'int1 < DT'2 \le T'int2$; $T'int2 < DT'3 \le T'int3$ and $T'int3 < DT'4 \le T'max$, where T'int1, T'int2 and T'int3 are intermediate temperatures ranging between T'min and T'max, such that T'int1 ranges between 420° C. and 480° C. and is preferably equal to 450° C., T'int2 ranges between 520° C. and 580° C. and is preferably equal to 550° C., and T'int3 ranging between 620° C. and 680° C. which is preferably equal to 650° C. These intermediate temperatures correspond to relative minima observed by the applicant on CO and $CO_2$ curves measured for samples from superficial deposits, notably soils of various nature and origins. Considering that, according to the literature, the combustion temperature is an approximation of thermal stability, the CO and $CO_2$ streams measured in the temperature ranges DT'1, DT'2 and DT'3 can be related to organic constituent classes of increasing stability. Considering that the thermal stability limit of calcite is close to T3, the $CO_2$ streams measured in temperature range DT'4 can be related to mineral carbon forms.

TABLE 2

| $DT'_0 \le T'min$ | $S4CO2_0$ | $S4CO_0$ |
|---|---|---|
| $T'min < DT'_1 \le T'int1$ | $S4CO2_0$ | $S4CO_1$ |
| $T'int1 < DT'_2 \le T'int2$ | $S4CO2_2$ | $S4CO_2$ |
| $T'int2 < DT'_3 \le T'int3$ | $S4CO2_3$ | $S4CO_3$ |
| $T'int3 < DT'_4 \le T'max$ | $S4CO2_4$ | $S4CO_4$ |

3—Characterization and Quantification of the Carbon Present in the Sample

This step characterizes and quantifies the carbon present in the soil sample, and notably is for determining at least one of an organic carbon content and a mineral carbon content. This step comprises at least the two substeps detailed hereafter.

3.1 Determination of a Parameter Characterizing the Mineral Carbon Proportion in the Sample According to the invention, this first substeps goal is to determine a parameter characterizing the proportion of mineral carbon in relation to the total carbon present in the sample considered, from the quantity of CO2 measured in step 2 described above.

More precisely, according to the invention, a parameter Scmin, representative of a proportion of mineral carbon in relation to the total carbon in the sample, is determined from a ratio between the quantity of $CO_2$ released by the sample residue above the intermediate temperature T'int3 of the heating sequence in an oxidizing atmosphere ranging between 620° C. and 680° C. (defined in step 2), and the total quantity of $CO_2$ released by this residue during the heating sequence in an oxidizing atmosphere. Thus, parameter SCmin is defined by the proportion of $CO_2$ released by thermal decomposition of the mineral carbon contained in the sample during the heating sequence in an oxidizing atmosphere, in relation to the total quantity of $CO_2$ released during this heating sequence, in an oxidizing atmosphere.

According to an implementation of the invention, parameter SCmin is determined according to a formula of the type:

$$SCmin = \frac{S4CO2_4}{S4CO2_t}$$

where $$S4CO2_t = \sum_{i=0}^{i=4} S4CO2_i$$

where terms $S4CO2_i$, with i ranging from 1 to 4, defined in the previous step. In general, term $S4CO2_4$ very predominantly corresponds to the $CO_2$ released by decomposition of the carbonate mineral species and $S4CO2_1$ corresponds to the total $CO_2$ stream during the oxidation phase.

According to the invention, a threshold value is defined for parameter SCmin, which below may be considered with the soil sample being devoid of mineral form (i.e. it is a non-carbonate sample) or, in other words, below which it may be considered that any carbon form contained in this sample which is of organic nature.

According to an implementation of the invention, the threshold value of parameter SCmin, denoted by SCmin_seuil, according to which the soil sample considered, is devoid of mineral form, which can range between 0.03 and 0.05, and it is preferably equal to 0.04. These values correspond to errors related to the implementation of the method of the invention, due to the measuring device itself and to the determination of quantities of $CO_2$ released in the temperature ranges DT'i defined in Table 2.

According to an implementation of the invention, the carbon of a sample can further be characterized by defining four abundance classes for the mineral forms of carbon of a sample, with the abundance classes being defined according to the value of parameter SCmin of the invention as follows:

if SCmin<0.04: the sample comprises no mineral form of carbon;

if 0.04<SCmin<0.2: the sample comprises mineral forms of carbon as traces;

if 0.2<SCmin<0.6: the sample comprises mineral forms of carbon; and if SCmin>0.6: the sample comprises mineral forms of carbon in abundance.

3.2 Determination of at Least One of an Organic Carbon Content and a Mineral Carbon Content This step determines at least one of an organic carbon content and a mineral carbon content from the quantities of HC, CO and $CO_2$ measured in steps 1 and 2 as described above, and according to the value of parameter SCmin described in substep 3.1 above.

According to an implementation of the invention, new parameters denoted by TOCfs and MinCfs hereafter, which are specific to the heating sequences in an inert atmosphere and in an oxidizing atmosphere according to the invention, which are dedicated to samples from a superficial deposit, which are defined. Parameters TOCfs and MinCfs according to the invention respectively represent the organic carbon content and the mineral carbon content of a sample from a superficial deposit, unlike the conventional parameters TOC and MinC defined in the prior art, which are not suitable for superficial deposit samples. Moreover, according to the invention, the formulas for determining parameters TOCfs and MinCfs which are defined depend on the value of parameter SCmin in relation to the threshold value SCmin_seuil defined in the previous substep.

According to the invention, two possible cases are defined depending on the value of parameter SCmin:

a) First Case: SCmin≤SCmin_Seuil

According to the invention, if the value of parameter SCmin is less than threshold value SCmin_seuil defined in the previous substep (i.e. if the sample considered is a non-carbonate sample), the mineral carbon content is zero and the organic carbon content depends on the total quantities of HC, CO and $CO_2$ released during the heating sequence in an inert atmosphere, and on the quantities of CO and $CO_2$ released during the heating sequence in an oxidizing atmosphere up to the intermediate temperature T'int3 defined above.

Thus, contrary to what is taught by the prior art, which calculates a non-zero parameter MinC even in the absence of mineral carbon in the sample, the present invention allows determination of a mineral carbon content representative of the real mineral carbon content of a sample of a superficial deposit without a mineral form of carbon. In addition, the organic carbon content according to the invention is determined by accounting for, unlike the prior art, of the total quantities of CO and $CO_2$ released during the heating sequences in an inert atmosphere and in an oxidizing atmosphere. Indeed, determination of the organic carbon content according to the prior art only considers the quantities of CO and $CO_2$ released below temperature T2 of the heating sequence in an inert atmosphere defined in step 1, with half of the quantity of CO being released above temperature T2 of the heating sequence in an inert atmosphere defined in step 1, and the quantities of CO and $CO_2$ released below intermediate temperature T'int3 of the heating sequence in an oxidizing atmosphere defined in step 2.

According to an implementation of the invention, if the value of parameter SCmin is less than threshold value SCmin_seuil defined in the previous substep, parameters MinCfs and TOCfs respectively representing the mineral carbon content and the organic carbon content of a superficial deposit sample can further be defined according to the following formulas:

MinCfs=0;

TOCfs=PCfs+RCfs, where PCfs is a parameter representative of the pyrolyzed organic carbon content of a superficial deposit and RCfs is a parameter representative of the residual organic carbon content of a superficial deposit. These contents are defined by formulas specific to the heating sequences in an inert atmosphere and in an oxidizing atmosphere according to the invention, which can be written as follows:

$$PCfs = (S2_t \times 0.083) + \left(S3CO2_t \times \frac{12}{440}\right) + \left(S3CO_t \times \frac{12}{280}\right);$$

$$RCfs = \left(S4CO2_a \times \frac{12}{440}\right) + \left(S4CO_a \times \frac{12}{280}\right);$$

with:

$$S2_t = \sum_{i=0}^{i=6} S2_i;\ S3CO2_t = \sum_{i=0}^{i=6} S3CO2_i;\ S3CO_t = \sum_{i=0}^{i=6} S3CO_i;$$

$$S4CO2_a = \sum_{i=0}^{i=3} S4CO2_i\ \text{and}\ S4CO_a = \sum_{i=0}^{i=3} S4CO_i.$$

b) Second Case: SCmin>SCmin_Seuil

According to the invention, if the value of parameter SCmin is greater than threshold value SCmin_seuil defined in the previous substep (i.e. the sample considered is a carbonate sample), a preliminary assessment is performed of a quantity of CO2 released by thermal cracking of the organic matter contained in the sample during the heating sequence in an inert atmosphere above temperature T2 defined in step 1.

According to the invention, this quantity of $CO_2$ released by thermal cracking of the organic matter during the pyrolysis phase above temperature T2, denoted by $S3CO2_c$ hereafter, is assessed from the quantity of $CO_2$ released during the heating sequence in an inert atmosphere up to temperature T2, denoted by S3CO2a which hereafter is multiplied by a predefined factor k, which can be written with a formula of the type:

$$S3CO2_c = k \times S3CO2_a$$

According to a first implementation of the invention, the value of predefined factor k ranges between 1.3 and 1.4, and it is preferably equal to 1.3724.

According to a second implementation of the invention, the value of predefined factor k can be determined experimentally, by plural (at least 10, preferably at least 50) samples from non-carbonate superficial deposits, for which at least the heating sequence in an inert atmosphere according to the invention is applied to each sample of the plural samples, and a quantity of $CO_2$ released by each sample during this heating sequence in an inert atmosphere is continuously measured; and factor k is determined by a linear regression applied between the quantities of $CO_2$ released by samples up to temperature T2 of the heating sequence in an inert atmosphere defined in step 1 and the quantities of $CO_2$ released by the plurality of samples above this temperature T2. Moreover, the samples from superficial deposits without mineral carbon form have a remarkable property which is the quantities of $CO_2$ released during the heating sequences in an inert atmosphere above and below limit temperature T2 are linearly correlated. In other words, the total quantity of $CO_2$ released at a temperature greater than limit temperature T2 is k times the total quantity of $CO_2$ released at a temperature less than limit temperature T3, which can be expressed with a formula of the type:

$$\sum_{i=3}^{i=6} S3CO2_i = k \times \sum_{i=0}^{i=2} S3CO2_i,$$

where k is established for samples having SCmin≤SCmin_seuil. According to this implementation of the invention, the value of this factor k, predefined from samples without mineral form which can be generalized to the case of samples with mineral carbon forms (i.e. if SCmin is greater than threshold value SCmin_seuil). Indeed, considering that the organic carbon source is in first approximation comparable for non-carbonate soils and carbonate soils, it is reasonable to consider that the distribution of labile compounds in relation to compounds thermally stable above the threshold temperatures is comparable for both types of samples.

In the case of a sample with mineral forms of carbon, the applicant has shown that the total quantities of $CO_2$ released above temperature T2 of the pyrolysis phase (that is parameter S3COb) cumulate in the streams resulting from thermal cracking of the organic matter (that is parameter S3COc) and those from the thermal decomposition of these mineral forms. Moreover, the higher the mineral carbon contents, the more negligible the contribution is of the thermally stable organic forms.

According to the invention, if the value of parameter SCmin is greater than threshold value SCmin_seuil defined in the previous substep, at least one of an organic carbon and mineral carbon content is determined by using the quantities of HC, CO and $CO_2$ measured during the heating sequence in an oxidizing atmosphere, which accounts for the quantity S3CO2c of $CO_2$ released by thermal cracking of the organic matter of the sample during the heating sequence in an inert atmosphere above temperature T2, previously assessed as described above.

According to an implementation of the invention, if the value of parameter SCmin is greater than threshold value SCmin_seuil defined in the previous substep, at least one of the organic carbon content can be determined from the total quantity of HC released during the heating sequence in an inert atmosphere, the quantity of CO released during the heating sequence in an inert atmosphere up to temperature T4, to which half of the quantity of CO released during the heating sequence in an inert atmosphere above this temperature T4 is added, the quantity of CO2 released during the heating sequence in an inert atmosphere up to temperature T2, to which the assessed quantity of CO2 released by thermal cracking of the organic matter during the heating sequence in an inert atmosphere above temperature T2 is added, and the quantities of CO and $CO_2$ released during the heating sequence in an oxidizing atmosphere up to intermediate temperature T'int3 predefined in step 2.

According to an implementation of the invention, if the value of parameter SCmin is greater than threshold value SCmin_seuil defined in the previous substep, a parameter TOCfs representing the organic carbon content of a superficial deposit sample can be defined with a formula of the type:

TOCfs=PCfs+RCfs, where PCfs is a parameter representative of the pyrolyzed organic carbon content of a superficial deposit sample and RCfs is a parameter representative of the residual organic carbon content of a superficial deposit. These contents are defined by formulas specific to the heating sequences in an inert atmosphere and in an oxidizing atmosphere according to the invention, which can be written as follows:

$$PCfs = (S2_t \times 0.083) +$$
$$\left([S3CO2_a + S3CO2_c] \times \frac{12}{440}\right) + \left([S3CO_a + 1/2S3CO_b] \times \frac{12}{280}\right)$$
$$RCfs = \left(S4CO2_a \times \frac{12}{440}\right) + \left(S4CO_a \times \frac{12}{280}\right)$$

and where $$S2_t = \sum_{i=0}^{i=6} S2_i;$$

$$S3CO2_a = \sum_{i=0}^{i=2} S3CO2_i;$$

$$S3CO2_b = \sum_{i=3}^{i=6} S3CO2_i;$$

$$S3CO2_c = k \times S3CO2_a$$

$$S3CO_a = \sum_{i=0}^{i=4} S3CO_i;$$

$$S3CO_b = \sum_{i=5}^{i=6} S3CO_i;$$

-continued $$S4CO2_a = \sum_{i=0}^{i=3} S4CO2_i;$$

$$S4CO_a = \sum_{i=0}^{i=3} S4CO_i.$$

According to an implementation of the invention, if the value of parameter SCmin is greater than threshold value SCmin_seuil defined in the previous substep, the mineral carbon content can be determined from the quantity of $CO_2$ released during the heating sequence in an inert atmosphere above temperature T2, from which the estimated quantity of $CO_2$ released by thermal cracking of the organic matter during the heating sequence in an inert atmosphere above temperature T2 is subtracted, from half of the quantity of CO released during the heating sequence in an inert atmosphere above temperature T4, and from the quantity of $CO_2$ released during the heating sequence in an oxidizing atmosphere above intermediate temperature T'int3.

According to an implementation of the invention, if the value of parameter SCmin is greater than threshold value SCmin_seuil defined in the previous substep, parameter MinCfs representing the mineral carbon content of a sample from a superficial deposit can be defined with a formula of the type:

$$MinCfs =$$

$$\left([S3CO2_b - S3CO2_c] \times \frac{12}{440}\right) + \left(1/2 S3CO_b \times \frac{12}{280}\right) + \left(S4CO2_b \times \frac{12}{440}\right)$$

$$\text{with } S3CO2_b = \sum_{i=3}^{i=6} S3CO2_i; \, S43CO2_c = k \times S3CO2_a;$$

$$S3CO_b = \sum_{i=5}^{i=6} S3CO_i; \, S4CO2_b = \sum_{i=3}^{i=4} S4CO2_i.$$

Thus, the definitions of the mineral carbon and organic carbon contents according to the invention account for the carbon forms present as follows: (i) all the carbon forms are organic in the samples such that SCmin<SCmin_seuil, and (ii) the other mineral carbon abundance classes comprise a thermally stable organic carbon part, plus a mineral carbon part, variable in nature as well as proportion.

Thus, after these two substeps, a reliable characterization and quantification of the carbon present in a superficial deposit sample is obtained via the determination of a parameter SCmin representing a proportion of mineral carbon in the sample, and the determination of the organic carbon and/or mineral carbon content of the sample, using for example parameters TOCfs and MinCfs specifically defined for carbonate and non-carbonate superficial deposits.

3.3 Determination of the Thermal Status of Organic Carbon Forms

This substep, which is optional, determines the thermal status of the organic carbon forms present in the sample. The thermal status of the organic carbon forms present in the sample is understood to be an indicator of the distribution of the various compound classes present in the sample, each defined by the cracking temperature thereof.

The organic matter of a soil is a complex heterogeneous mixture comprising constituents of various natures and origins which are residues from the gradual decomposition of the most labile biogenic constituents, free particles and constituents involved in organo-mineral complexes, and pyrogenic or petrogenic constituents. The thermal fractionation method according to the invention does not allow these specific constituents to be separated. On the other hand, it makes it possible to measure the contributions of compound classes defined each by their cracking temperature. Thermal stability being considered as a variable related to biogeochemical stability (i.e. the resistance to decomposition by micro-organisms), the contributions of the compound classes thus defined can be used to describe the heterogeneity of the organic matter of soils.

According to a first embodiment of this variant of the invention comprising a substep of determining the thermal status of the carbon forms of the sample, a decomposition index ID and a stability index IS can be defined from the contributions of the compound classes defined in previous steps 1 and 2 with formulas of the type:

decomposition index $ID = \log[S2_1 + S2_2]/S2_3$ stability index $IS = [S2_3 + S2_4 + S2_5 + S2_6]/100.$ Thus, these two indices are directly related to the most reactive fraction of the organic carbon (i.e. the pyrolyzed carbon part in form of hydrocarbon compounds).

Stability index IS measures the relative contributions of the thermally stable compound classes ($S2_3$, $S2_4$, $S2_5$ and $S2_6$) that are particularly abundant in superficial deposits and in the deep layers of soils, in contrast to the more labile compound classes ($S2_1$ and $S2_2$) that are more abundant in poorly decomposed plant tissues present in the organic layers and the superficial layers of soils.

Decomposition index ID measures the ratio of these most labile compound classes ($S2_1$ and $S2_2$) and the intermediate compound class ($S2_3$), which is particularly abundant in the organic and organo-mineral layers of soils. In general, decomposition index ID measures the degree of transformation of the organic matter as the compounds of the most labile compound classes are decomposed and the compounds of the most stable compound classes accumulate.

According to a second embodiment of this variant of the invention comprising a substep of determining the thermal status of the carbon forms of the sample, the thermal status of the carbon forms of a sample can be determined from the relative contributions of the various compound classes of a sample to calculate a thermally labile (i.e. resulting from thermal cracking and combustion below T3) organic carbon content and a thermally stable (i.e. resulting from thermal cracking and combustion below T3) organic carbon content.

According to an implementation of the invention, at least one of the following parameters characterizing the thermal status of the sample can be determined:

a thermally labile pyrolyzed organic carbon content, denoted by COPL, defined according to a formula of the type:

$$COPL (\% C) =$$

$$(S2_L \times 0.083) + \left([KCOPL * S3CO2_L] \times \frac{12}{440}\right) + \left(S3CO_L \times \frac{12}{280}\right)$$

with KCOPL ranging between 1 and 2, preferably equal to 1.3359 a thermally stable pyrolyzed organic carbon content, denoted by COPS, defined according to a formula of the type:

$$COPS\,(\%\,C) =$$

$$(S2_S \times 0.083) + \left( [KCOPS * S3CO2_L] \times \frac{12}{440} \right) + \left( [1/2S3CO_S] \times \frac{12}{280} \right)$$

with KCOPS ranging between 0.1 and 1, preferably equal to 0.6274 a thermally labile residual organic carbon content, denoted by CORL, defined according to a formula of the type:

$$CORL\,(\%\,C) = \left( S4CO2_L \times \frac{12}{440} \right) + \left( S4CO_L \times \frac{12}{280} \right)$$

a thermally stable residual organic carbon content, denoted by CORS, defined according to a formula of the type:

$$CORS\,(\%\,C) = \left( S4CO2_S \times \frac{12}{440} \right)$$

where $S2_L = \sum_{i=0}^{i=3} S2_i$; $S2_S = \sum_{i=4}^{i=6} S2_i$ $S3CO2_L = \sum_{i=0}^{i=3} S3CO2_i$; $S3CO2_S = \sum_{i=4}^{i=6} S3CO2_i$;

$S3CO_L = \sum_{i=0}^{i=4} S3CO_i$; $S3CO_S = \sum_{i=5}^{i=6} S3CO_i$;

$S4CO2_L = \sum_{i=0}^{i=1} S4CO2_i$; $S4CO2_S = \sum_{i=2}^{i=3} S4CO2_i$;

$S4CO_L = \sum_{i=0}^{i=1} S4CO_i$; $S4CO_S = \sum_{i=2}^{i=3} S4CO_i$.

These partial contents are particularly useful to understand the dynamics of organic matter in soils, because they allow comparison of the total organic carbon stocks with the contributions of the various carbon forms, and to monitor the evolution of these stocks over time. They notably allow exploration of the relations between the thermally labile organic carbon and the thermally stable organic carbon stocks that are directly correlated in soils, which indicates that transfer from one stock to the other actually takes place in the soils.

EXAMPLES

The features and advantages of the method according to the invention will be clear from reading the application example hereafter.

The method according to the invention was applied to a series of 9 distinct soil samples, denoted by ECHSi hereafter, i ranging from 1 to 9, samples ECHS2, ECHS3, ECHS8, ECHS9 coming from carbonate soils, and samples ECHS1, ECHS4, ECHS5, ECHS6, ECHS7 coming from non-carbonate soils.

The method according to the invention was further applied to a series of 7 distinct peat samples, denoted by ECHTi hereafter, with i=1 to 7, coming from the same peat sequence and dating back to 340, 2850, 4540, 5220, 6050, 8850 and 9640 years.

FIG. 4A (respectively FIG. 4B) shows a histogram comparing the values of the organic carbon contents Corg (respectively the mineral carbon contents Cmin) determined by the method according to the invention and by the prior art for each of the 9 soil samples ECHS1 to ECHS9. More precisely, FIG. 4A (respectively FIG. 4B) shows the values (light gray bars on the right) of parameter TOCfs (respectively MinCf) according to the invention and the values (dark gray bars on the left) of parameter TOC (respectively MinC) according to the prior art for each of these 9 samples. In general, the values of TOCfs are globally higher (by about 8%) than the values of TOC according to the prior art, which corresponds to the proportion of organic carbon considered wrongly as mineral in the prior art. It is also noted that the values of MinCfs are markedly lower than values MinC for the non-carbonate soil samples for which the value of MinC according to the prior art corresponds to streams of CO and $CO_2$ released during pyrolysis and oxidation of organic forms of carbon. It can also be noted that the values of MinCfs are closer or even identical to that of MinC for the carbonate soil samples for which the proportion of organic carbon is wrongly counted in the value of MinC according to the prior art is lower than in non-carbonate soils, or even negligible if the organic carbon forms are entirely pyrolyzed and oxidized below the threshold temperatures used to calculate MINC according to the prior art.

FIG. 5A (respectively FIG. 5B) shows a histogram comparing the values of the organic carbon contents Corg (respectively the mineral carbon contents Cmin) determined by the method according to the invention and by the prior art for each of the 7 peat samples ECHT1 to ECHT7. More precisely, FIG. 5A (respectively FIG. 5B) shows the values (light gray bars on the right) of parameter TOCfs (respectively MinCf) according to the invention and the values (dark gray bars on the left) of parameter TOC (respectively MinC) according to the prior art for each of these 7 samples. It is noted in this figure that the values of TOC (respectively MinC) and of TOCfs (respectively MinCfs) are markedly higher (respectively lower) since, for these organic samples, nearly all of the carbon taken into account to calculate MINC according to the prior art actually results from the pyrolysis and the oxidation of organic compounds.

Thus, the present invention allows reliable characterization and quantification of the carbon forms present in a sample of a superficial deposit, whether the superficial deposit is a carbonate deposit or not. In particular, the present invention defines heating sequences in an inert atmosphere and in an oxidizing atmosphere suited to superficial deposits, and at least one of organic carbon and mineral carbon contents accounting for an estimated quantity of $CO_2$ released by thermal cracking of the organic matter of the sample during the heating sequence in an inert atmosphere above temperature T2.

The invention claimed is:

1. A method of characterizing and quantifying carbon present in a superficial deposit, from a sample representative of the superficial deposit, comprising:

A. heating the sample according to a first heating sequence in an inert atmosphere, and continuously measuring a quantity of hydrocarbon compounds, a quantity of CO and a quantity of $CO_2$ released during the first heating sequence, the first heating sequence in an inert atmosphere comprising at least a succession of at least six isothermal stages of predetermined duration, the succession of the at least six isothermal stages comprising a first isothermal stage at a first temperature ranging between 80° C. and 200° C. (T0), a second isothermal stage at a second temperature ranging between 340° C. and 380° C. (T1), a third isothermal stage at a third temperature ranging between 400° C. and 440° C. (T2), a fourth isothermal stage at a fourth temperature ranging between 450° C. and 490° C. (T3), a fifth isothermal stage at a fifth temperature ranging between 500° C. and 540° C. (T4), and a sixth isothermal stage at a sixth temperature ranging between 580° C. and 650° C. (T5), the isothermal stages being connected by a thermal gradient;

B. heating a residue of the sample from the first heating sequence according to a second heating sequence in an oxidizing atmosphere, and measuring a quantity of CO and a quantity of $CO_2$ released during the second heating sequence, the second heating sequence in an oxidizing atmosphere starting at a minimum temperature ranging between 150° C. and 300° C., and ending at a maximum temperature ranging between 850° C. and 1200° C., following a thermal gradient;

C. determining a value of a parameter SCmin representative of a mineral carbon proportion in relation to total carbon of the sample, from a ratio between a quantity of $CO_2$ released by the residue of the sample above an intermediate temperature of the second heating sequence ranging between 620° C. and 680° C., and a quantity of $CO_2$ released by the residue during the second heating sequence;

D. quantifying at least one of an organic carbon content and a mineral carbon content of the sample by:
i. if the value of the parameter SCmin is less than or equal to a predefined threshold value of the parameter SCmin, the mineral carbon content is zero and the organic carbon content depends on a totality of the quantities of HC, CO and $CO_2$ released during the first heating sequence, and on quantities of CO and $CO_2$ released during the second heating sequence up to an intermediate temperature of the second heating sequence;
ii. if the value of the parameter SCmin is greater than the predefined threshold value of the parameter SCmin:
a quantity of $CO_2$ released by thermal cracking of the organic matter of the sample during the first heating sequence above the third temperature (T2) is estimated from the quantity of $CO_2$ released during the first heating sequence up to the third temperature (T2) of the first heating sequence, multiplied by at least a predefined factor k; and
the organic carbon content and the mineral carbon content are determined according to the quantities of HC, CO and $CO_2$ released during the first heating sequence and to the quantities of CO and $CO_2$ released during the second heating sequence up to the intermediate temperature of the second heating sequence, and by accounting for the estimated quantity of $CO_2$ released by thermal cracking of the organic matter of the sample during the first heating sequence above the third temperature (T2).

2. A method as claimed in claim 1, wherein, if the value of the parameter SCmin is greater than the predefined threshold value of the parameter SCmin then:
the organic carbon content depends on a totality of the quantity of HC released during the first heating sequence, on a quantity of CO released during the first heating sequence up to the fifth temperature to which half of a quantity of CO released during the first heating sequence above the fifth temperature is added, on a quantity of $CO_2$ released during the first heating sequence up to the third temperature to which an estimated quantity of $CO_2$ released by thermal cracking of the organic matter of the sample during the first heating sequence above the third temperature is added, and on quantities of CO and $CO_2$ released during the second heating sequence up to the intermediate temperature of the second heating sequence; and
the mineral carbon content depends on a quantity of $CO_2$ released during the first heating sequence above the third temperature of the first heating sequence from which an estimated quantity of $CO_2$ released by thermal cracking of the organic matter of the sample during the first heating sequence above the third temperature is subtracted, on the half of the quantity of CO released during the first heating sequence above the fifth temperature, and on a quantity of $CO_2$ released during the second heating sequence above the intermediate temperature of the second heating sequence.

3. A method as claimed in claim 2, wherein the predefined factor k ranges between 1.3 and 1.4.

4. A method as claimed in claim 3, wherein the predefined factor k is 1.3724.

5. A method as claimed in claim 2, wherein, when using samples from non-carbonate superficial deposits, at least the first heating sequence is applied to each of the samples, a quantity of $CO_2$ released by each of the samples during the first heating sequence is measured, and the factor k is determined by using a linear regression applied between the quantities of $CO_2$ released by the samples up to the third temperature of the first heating sequence and the quantities of $CO_2$ released by the samples above the third temperature of the first heating sequence.

6. A method as claimed in claim 2, wherein the threshold value is 0.04.

7. A method as claimed in claim 2, wherein a duration of isothermal stages of the first heating sequence ranges between 3 and 5 minutes.

8. A method as claimed in claim 7, wherein the first heating sequence ranges between 20° C. and 25° C. min[-1].

9. A method as claimed in claim 1, wherein the predefined factor k ranges between 1.3 and 1.4.

10. A method as claimed in claim 9, wherein the predefined factor k is 1.3724.

11. A method as claimed in claim 1, wherein, when using samples from non-carbonate superficial deposits, at least the first heating sequence is applied to each of the samples, a quantity of $CO_2$ released by each of the samples during the first heating sequence is measured, and the factor k is determined by using a linear regression applied between the quantities of $CO_2$ released by the samples up to the third temperature of the first heating sequence and the quantities of $CO_2$ released by the samples above the third temperature of the first heating sequence.

12. A method as claimed in claim 1, wherein the threshold value of the parameter SCmin ranges between 0.03 and 0.05.

13. A method as claimed in claim 12, wherein the threshold value is 0.04.

14. A method as claimed in claim 1, wherein the first temperature (T0) of the first heating sequence ranges between 80° C. and 150° C.

15. A method as claimed in claim 14, wherein the first heating sequence is 150° C.

16. A method as claimed in claim 1, wherein the minimum temperature of the second heating sequence is equal to the first temperature (T0) of the first heating sequence.

17. A method as claimed in claim 1, wherein a duration of the isothermal stages of the first heating sequence ranges between 3 and 5 minutes.

18. A method as claimed in claim 1, wherein one thermal gradient of the first heating sequence ranges between 1° C. and 50° C. min[-1].

19. A method as claimed in claim 1, wherein a thermal gradient of the second heating sequence ranges between 20° C. and 40° C. min$^{-1}$.

20. A method as claimed in claim 19, wherein the second heating sequence ranges between 20° C. and 25° C. min$^{-1}$.

* * * * *